United States Patent
Abels et al.

(10) Patent No.: US 10,383,911 B2
(45) Date of Patent: Aug. 20, 2019

(54) STORAGE STABLE LYOPHILIZED TRIPEPTIDE FORMULATIONS

(71) Applicant: Dr. August Wolff Gmbh & Co. KG Arzneimittel, Bielefeld (DE)

(72) Inventors: Christoph Abels, Bielefeld (DE); Thorsten Christians, Bielefeld (DE); Ulrich Knie, Bad Salzuflen (DE)

(73) Assignee: Dr. August Wolff Gmbh & Co. KG Arzneimittel, Bielefeld (DE)

( * ) Notice: Subject to any disclaimer, the term of this patent is extended or adjusted under 35 U.S.C. 154(b) by 0 days.

(21) Appl. No.: 15/034,767

(22) PCT Filed: Oct. 27, 2014

(86) PCT No.: PCT/EP2014/072957
§ 371 (c)(1),
(2) Date: May 5, 2016

(87) PCT Pub. No.: WO2015/067493
PCT Pub. Date: May 14, 2015

(65) Prior Publication Data
US 2016/0279188 A1    Sep. 29, 2016

(30) Foreign Application Priority Data

Nov. 7, 2013 (EP) .................................... 13191934

(51) Int. Cl.
| | |
|---|---|
| A61K 38/06 | (2006.01) |
| A61K 9/19 | (2006.01) |
| C07K 5/09 | (2006.01) |
| A61K 47/12 | (2006.01) |
| A61K 9/20 | (2006.01) |
| A61K 8/64 | (2006.01) |
| A61K 9/16 | (2006.01) |
| A61K 9/50 | (2006.01) |
| A61Q 19/00 | (2006.01) |

(52) U.S. Cl.
CPC .............. *A61K 38/06* (2013.01); *A61K 8/64* (2013.01); *A61K 9/1611* (2013.01); *A61K 9/1617* (2013.01); *A61K 9/1623* (2013.01); *A61K 9/19* (2013.01); *A61K 9/2054* (2013.01); *A61K 9/2081* (2013.01); *A61K 9/5026* (2013.01); *A61K 47/12* (2013.01); *A61Q 19/00* (2013.01); *C07K 5/0815* (2013.01); *A61K 2800/10* (2013.01)

(58) Field of Classification Search
None
See application file for complete search history.

(56) References Cited

U.S. PATENT DOCUMENTS

| 8,003,608 B2 | 8/2011 | Luger et al. | |
|---|---|---|---|
| 2008/0188544 A1* | 8/2008 | Potts | A61K 9/19 514/421 |
| 2009/0118196 A1* | 5/2009 | Crockford | A61K 9/0048 514/1.1 |

FOREIGN PATENT DOCUMENTS

| EP | 0335662 | 10/1989 |
|---|---|---|
| WO | WO1989/09226 A1 | 10/1989 |
| WO | WO2006/138708 A1 | 12/2006 |
| WO | WO2007/124090 A2 | 11/2007 |
| WO | WO2009/033806 A2 | 3/2009 |
| WO | WO-2009/065857 | 5/2009 |
| WO | WO2011/066291 A2 | 6/2011 |
| WO | WO-2013/041719 | 3/2013 |

OTHER PUBLICATIONS

Niu, C. et al., FDA perspective on peptide formulation and stability issues, *Journal of Pharmaceutical Sciences*, 87(11): 1331-34, Nov. 1, 1998.
Poole, S. et al., Peripheral Analgesic Activities of Peptides Related to Alpha-Melanocyte Stimulating Hormone and Interleukin-1Beta 193-195, *British Journal of Pharmacology*, 106: 489-92, Jan. 1, 1992.
Japanese Office Action for Japanese Patent Application No. 2016-528051, dated May 2, 2018.
English translation of Japanese Office Action for Japanese Patent Application No. 2016-528051, dated May 2, 2018.
Liu, J., Physical Characterization of Pharmaceutical Formulations in Frozen and Freeze-Dried Solid States: Techniques and Applications in Freeze-Drying Development, *Pharmaceutical Development and Technology*, 11: 3-28, 2006.
Карапетьянц М.Х., Дракин С.И Общая и неорганическая химия : Учебник для вузов ,-4-е изд., стер.-М.: Химия 2000, 592 с., стр. 59.
Russian Office Action for Russian Application No. 2016121401, dated Jan. 25, 2018.
English Translation of Russian Office Action for Russian Application No. 2016121401, dated Jan. 25, 2018.
Russian Search Report for Russian Application No. 2016121401.
ОПТИЧЕСКАЯ ИЗОМЕРИЯ И БИОЛОГИЧЕСКАЯ АКТИВНОСТЬ ЛЕКАРСТВЕННЫХ СРЕДСТВ И .Г. Смирнова ,Г.Н. Гильдеева, ,В.Г. Кукес . ВЕСТН. МОСК. У Н-ТА. СЕР. 2. ХИМИЯ , 2012. Т. 53. N 3, стр., 147.

* cited by examiner

*Primary Examiner* — James H Alstrum-Acevedo
*Assistant Examiner* — Tara L Martinez
(74) *Attorney, Agent, or Firm* — Julie K. Staple; Dinsmore & Shohl LLP

(57) ABSTRACT

The invention relates to Lysyl-Prolyl-Threonine lyophilized formulations, in particular to L-Lysyl-D-Prolyl-L-Threonine lyophilized formulations, that are stable in storage, and to a process for preparing the lyophilized formulations. Moreover, the invention relates to pharmaceutical and cosmetic compositions comprising the lyophilized formulations, that are used in the therapeutic and/or prophylactic treatment, diagnosis and/or therapy of pain-related diseases, pruritus-related diseases, inflammatory diseases, and/or other diseases in a mammal.

24 Claims, 2 Drawing Sheets

STORAGE STABLE LYOPHILIZED TRIPEPTIDE FORMULATIONS

The invention relates to Lysyl-Prolyl-Threonine lyophilized formulations, in particular to L-Lysyl-D-Prolyl-L-Threonine lyophilized formulations, that are stable in storage, and to a process for preparing the lyophilized formulations. Moreover, the invention relates to pharmaceutical and cosmetic compositions comprising the lyophilized formulations, that are used in the therapeutic and/or prophylactic treatment, diagnosis and/or therapy of pain-related diseases, pruritus-related diseases, inflammatory diseases, and/or other diseases in a mammal.

The tripeptide Lysyl-Prolyl-Threonine (KPT, KdPT) has a chemical structure as shown in the following formula:

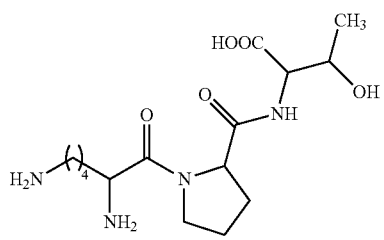

It is known in the art for being effective in the treatment of inflammatory diseases (WO 02/064131). The preparation of Lysyl-Prolyl-Threonine and its salts is described for example in EP 0 335 662 A1 being incorporated herein by reference. Moreover, Lysyl-Prolyl-Threonine is commercially available.

However, Lysyl-Prolyl-Threonine is highly hygroscopic and degrades easily under formation of a lysine-proline diketopiperazine. In addition Lysyl-Prolyl-Threonine shows a reduced stability in solution, in particular in aqueous solution, where it is sufficiently stable for at most one week under ambient conditions. These facts lead to a significantly reduced storage stability not only of the compound per se but also of medicaments containing it. Eventually significant concerns are created with regard to safety and efficacy of a medicament containing Lysyl-Prolyl-Threonine as an active ingredient.

Therefore, a need exists to provide for Lysyl-Prolyl-Threonine having an increased storage stability. In particular, a need exists to provide for Lysyl-Prolyl-Threonine in a form suitable to be administered as a medicament that remains safe and efficacious over an extended time period.

The object underlying the invention therefore is the provision of storage stable Lysyl-Prolyl-Threonine and medicaments containing it that remain safe and efficacious over an extended time period.

This object has surprisingly been solved in accordance with the present invention as indicated in the claims attached.

In particular, it has surprisingly been found out by the inventors that Lysyl-Prolyl-Threonine in lyophilized formulations (i.e. as a lyophilisate) shows an increased storage stability as compared to Lysyl-Prolyl-Threonine alone (i.e. non-lyophilized or lyophilized form). This finding is surprising since the lyophilisate, mainly containing the active ingredient Lysyl-Prolyl-Threonine in non-crystalline form due to lyophilsation, is more stable than Lysyl-Prolyl-Threonine alone that at least partly exists in crystalline form. This increased storage stability is even more surprising as Lysyl-Prolyl-Threonine in lyophilized formulations has a significantly higher surface area so that the skilled person actually would have expected a reduced storage stability. In other words, it was fully unexpected in the prior art that non-crystalline forms of Lysyl-Prolyl-Threonine also having a higher surface area are less susceptible to degradation into lysine-proline diketopiperazines and, consequently, are more storage stable than crystalline forms of Lysyl-Prolyl-Threonine.

Therefore, the subject-matter of the present invention is a lyophilized formulation comprising Lysyl-Prolyl-Threonine or a pharmaceutically acceptable salt thereof.

Further, according to the present invention the lyophilized formulation is for use as a medicament, preferably for use in the therapeutic and/or prophylactic treatment, diagnosis and/or therapy of pain-related diseases, pruritus-related diseases, inflammatory diseases, and/or other diseases.

Even further, the subject-matter of the present invention relates to a process for preparing the lyophilized formulation, and to the lyophilized formulation obtained by said process, wherein the process comprises the steps of:

(a) mixing the following components (in any suitable order): Lysyl-Prolyl-Threonine or a pharmaceutically acceptable salt thereof; an aqueous carrier; optionally one or more bulking agents; optionally one or more buffering agents; and optionally one or more pH adjusting agents; to provide for an aqueous preparation having a pH in the range of 3.0-5.0, wherein the free base of Lysyl-Prolyl-Threonine has a concentration of 0.1-175 mg/g, based on the aqueous preparation;

(b) lyophilizing the aqueous preparation to provide for the lyophilized formulation in solid form.

In a preferred embodiment the present invention relates to a process for preparing the lyophilized formulation, and to the lyophilized formulation obtained by said process, wherein the process comprises the steps of (in this order):

(a) mixing an aqueous carrier with one or more buffering agents;

(b) adding Lysyl-Prolyl-Threonine or a pharmaceutically acceptable salt thereof;

(c) adding one or more bulking agents and;

(d) optionally adding one or more pH adjusting agents;

to provide for an aqueous preparation having a pH in the range of 3.0-5.0, wherein the free base of Lysyl-Prolyl-Threonine has a concentration of 0.1-175 mg/g, based on the aqueous preparation;

(e) lyophilizing the aqueous preparation to provide for the lyophilized formulation in solid form.

The aqueous preparation may be a suspension/dispersion or solution. More preferably the steps (a) to (d) of the preferred embodiment are carried out under dissolution of the components so that the final aqueous preparation is an aqueous solution.

The lyophilisation step (e) may be carried out in vials, blisters or in any other larger vessel, such as stainless steel trays or tanks, so-called "bulk lyophilisation".

In addition, the present invention relates to a pharmaceutical or cosmetic composition comprising the lyophilized formulation and one or more pharmaceutical or cosmetic excipients.

Finally, the present invention relates to the non-therapeutic use of the lyophilized formulation as a cosmetic, preferably for the cosmetic treatment of the skin and/or mucosa of a mammal.

In the present invention the term "Lysyl-Prolyl-Threonine" means the tripeptide consisting of, in this order, the amino acids Lysine (Lys), Proline (Pro) and Threonine (Thr)

also known as KPT or KdPT (such as from WO 02/064131 or EP 0 335 662). It comprises (L)Lys-(D)Pro-(L)Thr, (L)Lys-(L)Pro-(D)Thr, (L)Lys-(D)Pro-(D)Thr, (L)Lys-(L) Pro-(L)Thr, (D)Lys-(D)Pro-(L)Thr, (D)Lys-(D)Pro-(D)Thr, (D)Lys-(L)Pro-(L)Thr, (D)Lys-(L)Pro-(D)Thr, or any mixtures thereof. (L)Lys-(D)Pro-(L)Thr is preferred.

According to the present invention Lysyl-Prolyl-Threonine may be present as the free base or in form of its pharmaceutically/cosmetically acceptable salts. Suitable pharmaceutically acceptable salts and/or cosmetically acceptable salts of the compounds according to the invention are chosen, for example, from the group consisting of chlorides, bromides, iodides, hydrochlorides, hydrobromides, sulfonates, methanesulfonates, sulfates, hydrogen sulfates, sulfites, hydrogen sulfites, phosphates, nitrates, methanoates, acetates, proprionates, lactates, citrates, glutarates, maleates, malonates, malates, succinates, tartrates, oxalates, fumarates, benzoates, p-toluenesulfonates and/or salts of amino acids, preferably the proteinogenic amino acids. The succinate, tartrate, oxalate, fumarate and acetate salts are preferred. The acetate salts are particularly preferred. Also suitable according to the invention are the solvates and/or hydrates thereof.

Lysyl-Prolyl-Threonine or its salts are present in the lyophilised formulation in an amount equivalent to 0.1-50 mg free base, based on 100 mg total weight of the lyophilized formulation. Preferred is an amount equivalent to 0.4-45 mg free base, more preferred of 0.4-40 mg free base, more preferred of 1-30 mg free base, even more preferred of 1-25 mg free base, based on 100 mg total weight of the lyophilized formulation.

The term "lyophilized formulation/lyophilisate" as used according to the invention generally means a formulation obtained by any lyophilisation and/or freeze drying process known in the art. It covers a formulation that comprises Lysyl-Prolyl-Threonine or its salts and other suitable excipients.

As the formulation according to the present invention is lyophilized, Lysyl-Prolyl-Threonine or its salts is present mainly in non-crystalline (amorphous) form. Crystallinity may be determined according to methods known in the art such as by X-ray diffraction or DSC.

The storage stability of Lysyl-Prolyl-Threonine or its salts according to the invention is determined by measuring the amount of lysine-proline diketopiperazine (DKP) being the main degradation product of Lysyl-Prolyl-Threonine. In general, the rate of increase over time of the amount of lysine-proline diketopiperazine in the lyophilized formulation or in the pharmaceutical/cosmetic compositions is indicative for the storage stability of Lysyl-Prolyl-Threonine. The higher the DKP amount is, the less storage stable is Lysyl-Prolyl-Threonine and/or the formulation containing it. The amount of lysine-proline diketopiperazine can be determined by common methods such as by HPLC (in particular Reversed Phase HPLC).

Preferably the lyophilized formulation according to the present invention comprises, as further suitable excipients, one or more bulking agents and/or one or more buffering agents and, optionally, one or more pH adjusting agents. The presence of a bulking agent and/or a buffering agent further increases the storage stability of Lysyl-Prolyl-Threonine in the lyophilized formulation. The optional pH adjusting agent additionally allows to regulate the pH value of the formulation within a specific pH range, preferably of pH 3-5. This leads to a further increase in storage stability.

Bulking agents according to the present invention are preferably selected from the group consisting of mannitol, sucrose, glycine, gelatin, hydroxypropyl starch, calcium carbonate and trehalose, and mixtures thereof. Particularly preferred are mannitol, sucrose and trehalose, or mixtures thereof, in particular a mixture of mannitol and trehalose. Most preferred is trehalose (e.g. in form of its dihydrate). Suitable amounts of bulking agent are 30-95 mg, preferably 40-90 mg, and more preferably 40-75 mg, based on 100 mg total weight of the lyophilised formulation.

Buffering agents according to the present invention are preferably selected from the group consisting of citric acid, sodium dihydrogenphosphate, acetic acid, succinic acid, glutamate, tris(hydroxymethyl) aminomethan (Tris) and histidine, and mixtures thereof. Particularly preferred are citric acid, sodium dihydrogenphosphate and histidine, most preferred is citric acid. Suitable amounts of buffering agent are 0.5-50 mg, preferably 1-20 mg, more preferably 2-18 mg, and even more preferably 5-15 mg, based on 100 mg total weight of the lyophilised formulation.

The pH adjusting agent according to the present invention is preferably selected from sodium hydroxide and hydrochloric acid. It allows to maintain the pH at a certain value. From a storage stability point of view the pH value of the lyophilized formulation preferably is 3.0-5.0, more preferably 3.5-4.5. Outside these ranges the storage stability significantly decreases. Suitable amounts of pH adjusting agent for adjusting the above pH values can be easily determined by the skilled person.

A particularly preferred embodiment according to the present invention is the combination of (L)Lys-(D)Pro-(L) Thr (preferably as acetate), trehalose or a mixture of trehalose and mannitol as the bulking agent and citric acid as the buffering agent. The lyophilisate may consist of only these components.

The compounds according to the invention can be prepared by a process comprising mixing, in any order, Lysyl-Prolyl-Threonine or a pharmaceutically acceptable salt thereof, an aqueous carrier, optionally one or more bulking agents, optionally one or more buffering agents, and optionally one or more pH adjusting agents, to provide for an aqueous preparation, followed by lyophilizing the aqueous preparation to provide for the lyophilized formulation in solid form. Preferably an aqueous carrier is first mixed with one or more buffering agents; then Lysyl-Prolyl-Threonine or a pharmaceutically acceptable salt thereof is added to the mixture, followed by the addition of one or more bulking agents. The aqueous preparation obtained in the mixing step usually has a pH in the range of 3.0-5.0, preferably in the range of 3.5 to 4.5, more preferably of 3.8-4.2. If necessary, one or more pH adjusting agents are added to adjust the pH to the above mentioned values. In the aqueous preparation the concentration (calculated as the free base) of Lysyl-Prolyl-Threonine is within the range of 0.1-175 mg/g, preferably of 0.5-150 mg/g, more preferably of 1-140 mg/g, more preferably of 2-100 mg/g, more preferably of 2-70 mg/g, even more preferably of 4-20 mg/g, based on the aqueous preparation. Further, if present, in the aqueous preparation the concentration of the bulking agent is within the range of 50-175 mg/g, preferably of 50-150 mg/g, more preferably of 50-140 mg/g, more preferably of 50-95 mg/g, more preferably of 52-80 mg/g, even more preferably of 55-75 mg/g, based on the aqueous preparation. In addition, if present, in the aqueous preparation the concentration of the buffering agent is within the range of 1-100 mg/g, preferably of 2-75 mg/g, more preferably of 2.5-40 mg/g, more preferably of 2.5-20 mg/g, more preferably of 3-15 mg/g, even more preferably of 3.5-9.5 mg/g, based on the aqueous preparation.

Aqueous carriers according to the present invention are those known in the prior art as suitable in lyophilisation processes. Preferred aqueous carriers are water and mixtures of water with suitable organic solvents such as alcohols (e.g., ethanol and/or n- or iso-propanol).

Lyophilisation according to the present invention may be carried out in conventional freeze-dryers (such as those of Hof Sonderanlagenbau, Lohra/Germany) using conventional conditions or in dynamic freeze-dryers (such as those of Meridion Technologies, Müllheim/Germany). The lyophilisates may be analyzed by scanning electron microscopy (SEM) to appraise their structure, and the total water content of the lyophilisates can be determined by colorimetric Karl-Fischer titration. The purity analysis may be done by RP HPLC.

The lyophilized formulation according to the present invention may be reconstituted with an aqueous carrier to form an aqueous preparation suitable to be administered as a medicament or cosmetic. The obtained aqueous preparation may be a solution or a suspension, preferably an aqueous solution. Reconstitution preferably is carried out by mixing the solid lyophilized formulation with the aqueous carrier. Particularly preferably reconstitution is done immediately before administration of the resulting aqueous preparation to a patient in need thereof. The reconstitution factor is defined as the ratio of the amount of lyophilized formulation (lyophilisate) and the amount of aqueous carrier. It preferably is between 1:0.5 to 1:1000, more preferably from 1:5 to 1:100 and most preferably from 1:10 and 1:60. The aqueous carriers used for reconstitution may be an aqueous solution that may contain further conventional pharmaceutically acceptable excipients such as flavouring agents, pH adjusting agents and/or preservatives. Most preferred for reconstitution of the lyophilisate is water. According to the invention the improved stability of the solid lyophilisate (indicated by a decreased amount of DKP as explained herein) also leads to an improved stability and quality of the aqueous preparation also containing the decreased amount of DKP as compared to KdPT solutions of the prior art.

Reconstitution of the lyophilized formulation preferably is done immediately before administration to a patient, namely 10 seconds to 20 minutes before administration, preferably 1 to 10 minutes before administration, more preferably 2 to 5 minutes before administration.

Instead of reconstitution the lyophilized formulation may alternatively be used as such or be mixed with one or more (solid) carrier substances or further pharmaceutical excipients/auxiliary substances to provide a (solid) pharmaceutical composition.

The lyophilized formulation according to the present invention may be used as a medicament, preferably for use in the therapeutic and/or prophylactic treatment, diagnosis and/or therapy of diseases chosen from the group comprising or consisting of pain-related diseases, pruritus-related diseases, inflammatory diseases, and/or other diseases.

The invention also provides the use of the lyophilized formulation according to the invention for the preparation of a medicament for therapeutic and/or prophylactic treatment, diagnosis and/or therapy of diseases chosen from the group comprising or consisting of pain- or pruritus-related diseases, inflammatory diseases, and/or other diseases.

The lyophilized formulation according to the invention can be used by itself or in combination with known substances for treatment of diseases chosen from the group comprising pain- or pruritus-related diseases, inflammatory diseases, and/or other diseases.

Pain-related diseases are chosen from the group comprising back pain, facial pain, headaches, migraine, joint pain, muscular pain syndromes, inflammatory pain-related diseases, neuropathic pain, peripheral pain, peripheral nerve damage, visceral pain, abdominal pain, menstruation symptoms, kidney- and gallstone pain, pruritus, cancer and tumor pain, sympathetic pain, postoperative pain, postraumatic pain, hyperalgesia and/or inflammatory pain.

Inflammatory diseases are chosen from the group comprising inflammatory diseases of the gastrointestinal tract, in particular inflammatory bowel diseases, such as Crohn's disease and/or colitis ulcerosa, acute or chronic inflammatory changes with inflammation of the gall bladder, inflammatory pseudopolyps, colitis cystica profunda, pneumatosis cystoides intestinales, pancreatitis, appendicitis, cardiovascular inflammation due to arthereosclerosis, ischemia, restenosis and/or vasculitis, sepsis, septicemia, allergies, asthma, Sjogren's syndrome, pulmonary inflammation, chronic airway inflammation, chronic obstructive pulmonary disease (COPD), tumor proliferation, tumor metastasis, transplant rejection, inflammatory diseases of the joints, such as rheumatoid arthritis, vulvovaginitis (all causes), and/or inflammatory diseases of the brain, skin, hair follicle, urogenital tract and of the eyes. Further inflammatory diseases comprise sinusitis, tenosynovitis, bursitis, tendonitis, lateral epicondylitis, adhesive cap sulitis, osteomyelitis, osteoarthritic inflammation, ocular inflammation, otitic inflammation and autoimmune inflammation.

Pruritus (itching) is a frequent symptom in skin therapy conventionally experienced as a type of pain stimulus. The itching sensation triggers the desire to scratch the affected area. Skin damaged by scratching further offers infectious pathogens a good nutrient medium and inflammations of scratched-open areas of skin are not infrequent. Pruritic skin and hair diseases are chosen from the group comprising pruritus, psoriasis, psoriatic arthritis, contact dermatitis, atopic eczema, scleroderma and other fibrotic diseases, systemic lupus erythematous, urticaria, lichen planus, lymphoma and/or allergic diseases or characterized by mast cell involvements.

The diseases in the sense of the present invention also comprise other diseases such as hyponatremia, edema, ileus, tussis, glaucoma, MS (multiple sclerosis), Morbus Parkinson and Morbus Alzheimer.

The organs involved in the pain- or pruritus-related diseases and/or inflammatory diseases are in particular the so-called barrier organs, namely the gastrointestinal tract, skin, lung, urogenital tract; the brain; the ear nose and throat tract; teeth; bones; liver; and hair. Particularly preferred embodiments of the invention relate to the treatment of the diseases of the bather organs.

Diseases of the gastrointestinal tract are chosen from the group comprising irritable bowel syndrome, gastric lesions, gastrointestinal ulcerations, exogenous and endogenous damage to the gastrointestinal mucosa, malfunctions of the gastrointestinal tract, adenomas, in particular in the intestine, and/or juvenile polyps.

Diseases of the lung (respiratory diseases) include inflammatory lung disease, obstructive lung diseases such as chronic obstructive pulmonary disease (COPD), restrictive lung diseases, respiratory tract infections such as upper respiratory tract infection, lower respiratory tract infection, malignant tumors and benign tumors, pleural cavity diseases, pulmonary vascular diseases, and neonatal diseases.

Diseases of the urogenital tract include analgesic nephropathy, bladder cancer, cystocele (fallen bladder), end stage renal disease (ESRD), glomerulonephritis, glomerulosclesis, goodpasture syndrome, hematuria (blood in the urine), hemolytic uremic syndrome, immunoglobulin A (IgA) nephropathy, impotence/erectile dysfunction, interstitial cystitis, kidney cancer, kidney stones, kidney transplantation, male factor infertility, nephrotic syndrome, neurogenic bladder, Peyronie's disease, and polycystic kidney disease.

Further diseases that may be treated with the compounds of the present invention are described in US 2011/0212882 A1 being incorporated herein by reference.

Preferably the lyophilized formulation and the pharmaceutical or cosmetic compositions containing the lyophilized formulation are used for the treatment and/or prophylaxis of inflammatory diseases of the skin, of inflammatory diseases of the gastrointestinal tract, of inflammatory diseases of the (blood) vessels, of autoimmune inflammation, allergic reactions and/or transplant rejections.

The lyophilized formulation according to the present invention may also be used as a cosmetic, namely for the non-therapeutic/cosmetic treatment of the skin and/or mucosa of a mammal.

The lyophilized formulation, either in solid form or in reconstituted form, according to the invention or compositions containing the lyophilized formulation can be administered systemically or topically. Preferably, the lyophilized formulation or compositions according to the invention are administered systemically in solid (either as such or be mixed with one or more (solid) carrier substances or further pharmaceutical excipients/auxiliary substances) or in reconstituted form, in particular in the form of an aqueous solution or suspension.

In the context of the present invention, the term "prophylactic treatment" is understood as meaning in particular that the lyophilized formulation according to the invention can be administered before symptoms of a disease occur or the risk of a disease exists.

The lyophilized formulation, either in solid form or as a reconstituted lyophilized formulation, preferably in the form of an aqueous solution or suspension, according to the invention can be administered according to conventional methods, for example orally, dermally, intranasally, transmucosally, pulmonally, enterally, buccally, rectally, intraurethral, aural, by inhalation, by means of injection, for example intravenously, parenterally, intraperitoneally, intradermally, subcutaneously and/or intramuscularly and/or locally, for example on painful areas of the body. Oral administration and administration by injection are particularly preferred. Oral administration is most preferred.

The lyophilized formulation according to the invention can be used in particular for the preparation of medicaments (pharmaceutical compositions) by being brought into a suitable dosage form together with at least one carrier substance or auxiliary substance. As mentioned above, one preferred form according to the invention is the reconstituted form with an aqueous carrier. In general suitable forms are, for example, injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules. It may also be used as stick packs or sachets.

Pharmaceutical dosage forms with delayed release (sustained release formulation) are furthermore preferred for oral administration of the compounds according to the invention. Examples of formulations with delayed release are sustained release matrix tablets, multilayered tablets, the coating of which can be, for example, constructed to be resistant to gastric juice, such as coatings based on shellac, sustained release capsules or formulations using biodegradable polymers, for example poly(lactic acid) polymers.

Conventional physiologically acceptable pharmaceutical or cosmetic auxiliary substances, preferably chosen from the group comprising carrier materials, fillers, solvents, diluents, wetting agents, emulsifiers, dyestuffs, preservatives, disintegrating agents, lubricants, salts for influencing the osmotic pressure, buffer substances, aromas and/or binders, can be added to the lyophilized formulation (either to the solid form or to the reconstituted aqueous preparation) and thus be used for the preparation of the pharmaceutical and cosmetic compositions.

The lyophilized formulation (and the pharmaceutical compositions containing it) according to the invention can be administered to the patients in need thereof for example one or more times a day, depending inter alia on the actual pharmaceutical dosage form, the way of administration and the disease to be treated.

In the following the present invention is described in more detail by making reference to specific examples.

EXAMPLES

1. Preparation of the Lyophilized Formulation of the Invention

About 60% of the water for injection required (WFI; 18-22° C.) was transferred into a glass beaker. The required amount of citric acid monohydrate was transferred into the beaker and dissolved stirring constantly. The required amount of the active ingredient KdPT-acetate was transferred into the beaker and dissolved, stirring constantly. The required amount of trehalose dihydrate was transferred into the beaker and dissolved stirring constantly. The pH-value was measured and corrected, if necessary, with 1 M sodium hydroxide solution to pH 3.8-4.2. Values above 4.2 were not corrected. The formulation was filled up with WFI to final weight. The pH-value was checked and corrected, if necessary, with 1 M sodium hydroxide solution to pH 3.8-4.2. Values above 4.2 were not corrected. Filtration with a 0.2 µm PTFE filter. Detailed compositions of formulated aqueous preparations are as follows:

TABLE 1

|  | 20 mg/g |
|---|---|
| KdPT-free base | 20.0 mg |
| Citric acid monohydrate | 9.2 mg |
| Trehalose dihydrate | 55.26 mg |
| Sodium hydroxide solution 1M | q.s. |
| Water for injection | ad 1000.0 mg |

TABLE 2

| | 10 mg/g |
|---|---|
| KdPT-free base | 10.0 mg |
| Citric acid monohydrate | 9.2 mg |
| Trehalose dihydrate | 55.26 mg |
| Sodium hydroxide solution 1M | q.s. |
| Water for injection | ad 1000.0 mg |

TABLE 3

| | 4 mg/g |
|---|---|
| KdPT-free base | 4.0 mg |
| Citric acid monohydrate | 9.2 mg |
| Trehalose dihydrate | 55.26 mg |
| Sodium hydroxide solution 1M | q.s. |
| Water for injection | ad 1000.0 mg |

Vials were washed in an ultrasonic bath for 15 minutes in pure water. Afterwards the vials were dried and depyrogenized at 300° C. for 2 hours. After cooling off the vials were filled with the corresponding aqueous preparation indicated in the Tables 1-3 above by pipetting, and stoppers were set in lyophilization position. Filled vials were transferred into the freeze dryer (from Hof Sonderanlagenbau). A thermo shield of two lines empty vials was introduced to minimize external temperature influences on the filled vials during lyophilization. Solutions in the vials were lyophilized Afterwards the freeze-drying chamber was vented to 500 mbar with nitrogen and vials were closed. After venting to atmospheric pressure the vials were capped and stored at 5° C.

The process data of the lyophilization, e.g. pressure and shelf temperature, were logged by a controlling computer and visualized in a graph. Thermo couple monitoring inside the vials during the lyophilization process helped to detect the necessary drying time.

The lyophilisates were examined in the glass vials. In the development runs lyophilisates were removed from the vial and broken in radial section to inspect the interior.

Figure 1:
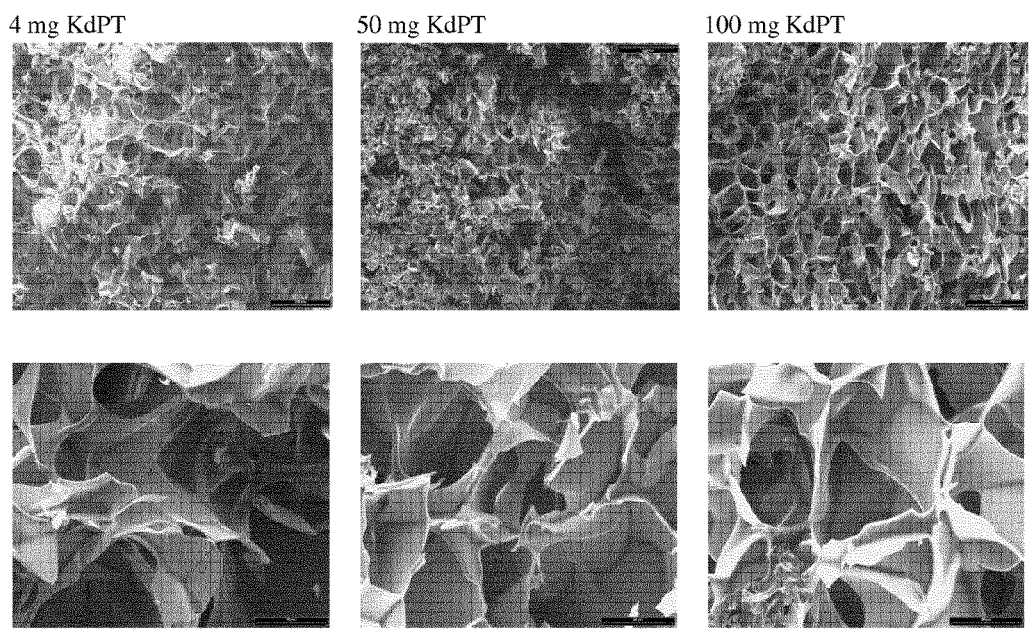
FIG. 1 shows Scanning Electron Microscopy images of lyophilisates obtained by lyophilization of aqueous preparations containing 4 mg/g, 10 mg/g and 20 mg/g KdTP base, respectively. The three images in the upper row were obtained with 100× magnification; the three images in the lower row were obtained with 500× magnification. The images show the non-crystalline (amorphous) form of the lyophilisates having a sponge-like structure.
Figure 2:
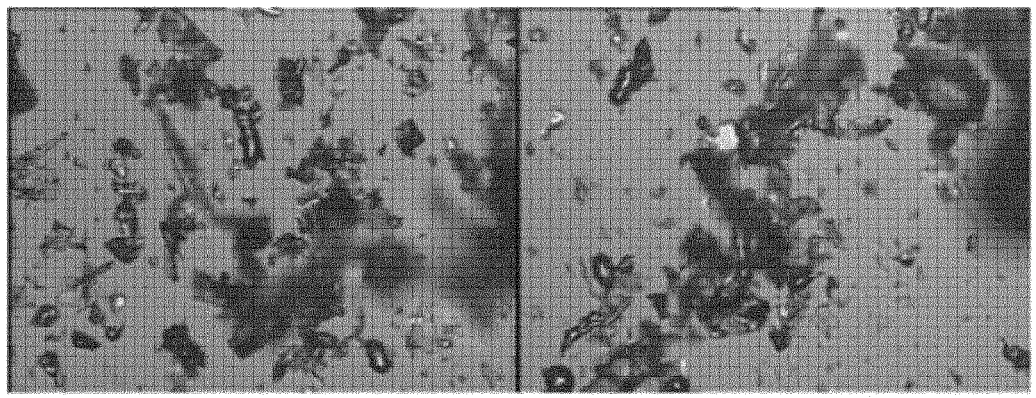
FIG. 2 shows Light Microcopy images of KdPT-acetate alone in crystalline form.

Lyophilisates were analyzed via SEM to appraise their structure. With SEM it is possible to detect minor defects of lyophilisates which are not visible to the naked eye. Lyophilisates were broken, and the vertical breakage was sputtered with a thin gold layer in a $10^{-1}$ mbar argon atmosphere at a sputter current of 20 mA for 30 seconds. The distance between the sample and the gold source was about 8 cm. Analysis via SEM was performed with 50×, 100×, 250× and 500× magnification. Some of the results are shown in FIG. 1.

2. Stability Measurement of Lyophilized Formulation of the Invention

The stability of the inventive three lyophilisates obtained from the aqueous preparations in Tables 1-3 (Example 1: 20 mg/g, Example 2: 10 mg/g and Example 3: 4 mg/g) as described above under 1. is determined by measuring therein the amount of lysine-proline diketopiperazine (DKP) by HPLC over a storage period of 24 months at 25° C. The results are shown in Table 4. For comparative purposes the same measurement was done with the solid compound KdPT alone. The results are shown in Table 5. The amount of DKP in all examples and comparative examples is in correlation with the stability of KdPT, i.e. the higher the DKP amount, the less stable the KdPT.

The HPLC measurement was carried out under the following conditions:
Column: Synergi Hydro RP (4 μm) 80 Å 250×4.6 mm
Eluent: A: perchloric acid in water
B: perchloric acid in water/acetonitrile
Gradient:

| Time (min) | Eluent A (%) | Eluent B (%) |
|---|---|---|
| 0 | 100 | 0 |
| 30 | 98 | 2 |
| 42 | 98 | 2 |
| 52 | 0 | 100 |
| 62 | 100 | 0 |
| 72 | 100 | 0 |

Injection volume: 25 μl
Flow rate: 1.0 ml/min
Oven temperature: 30° C.
Autosampler temperature: 5° C.
Detection: UV 220 nm
The following results were obtained:

TABLE 4

(Inventive Examples 1-3)

| | 0 months | 3 months | 6 months | 9 months | 12 months | 18 months | 24 months |
|---|---|---|---|---|---|---|---|
| Ex. 1 | 0.4 | 0.5 | 0.5 | 0.5 | 0.5 | 0.6 | 0.8 |
| Ex. 2 | 0.4 | 0.4 | 0.4 | 0.5 | 0.6 | 0.6 | 0.6 |
| Ex. 3 | 0.4 | 0.4 | 0.4 | 0.5 | 0.5 | 0.6 | 0.4 |

The data obtained are % values of DKP based on the amount of KdPT free base.

It becomes evident from Table 4 that the amounts of DKP measured over a time period of 24 months remains almost constant in all Examples 1-3 (Ex. 1: 0.4 to 0.8%; Ex. 2: 0.4 to 0.6%; Ex. 3: 0.4 to 0.4%). These results clearly show the storage stability of KdPT in form of the lyophilisates according to the invention.

TABLE 5

(Comparative Example 1)

| Comp. Ex. 1 | 0 months | 3 months | 6 months | 9 months | 12 months | 18 months | 24 months |
|---|---|---|---|---|---|---|---|
| (%) | 0.7 | 1.7 | 2.1 | 2.4 | 3.9 | 3.6 | 4.5 |

The data obtained are % values of DKP based on the amount of KdPT free base.

It becomes evident from Table 5 that the amounts of DKP measured over a time period of 24 months significantly increased in Comparative Example 1 (Comp. Ex. 1: 0.7 to 4.5%). In addition, the white powder after 12 months became yellowish showing the increased amounts of DKP impurities upon gradual degradation of KdPT. These results clearly show the reduced storage stability of the solid compound KdPT according to the prior art.

3. Direct Compression (Comparative Example 2)
3.1 Process

Instead of lyophilisation a direct compression of KdPT with suitable excipients was carried out. For direct compression a final blend is manufactured containing KdPT, excipients for direct compression, disintegrants and glidant/lubricants (cf. below). This formulation was then compressed on an eccentric press using 9 mm diameter punches (convex) to the respective weight.

3.2 Formulations

Direct compression (DC) trials were performed using different excipients typically used for direct compression. The following DC-excipients were used:
MCC 101 (microcrystalline cellulose)
Sorbitol DC
Galen IQ 720 (isomalt)
Trehalose
Mannitol 200 DC These excipients were used in approximately the 3- to 4-fold amount compared to KdPT. Additionally silicon dioxide and magnesium stearate were added to the final blend for compression in the usual quantities. A disintegrant (Croscarmellose) was added to the formulation to achieve a satisfying disintegration time. The target tablet mass was for all formulations approximately 250-270 mg.

The formulations were additionally coated to increase the stability of KdPT in the finished tablet. As the coating polymer PVA (polyvinyl alcohol) was used. The quality used was the ready-to-use-system Opadry II white from Colorcon. The amount of polymer applied was approximately 4% which is the usual amount of coating applied to achieve a water vapour resistant layer.

The coating trials were performed using the laboratory coater Glatt GC 300 for a batch size of approximately 1.2 to 1.4 kg.

The following tablet sample was manufactured by direct compression following the process as described above. Additionally a coating was applied on PVA base (i.e. ready-to-use system Opadry II white) as a water vapour barrier.

TABLE 6

| Compound | Function | Amount mg/unit |
|---|---|---|
| KdPT | API | 63.61* |
| MCC 101 | Filler | 177.89 |
| Syloid AL-1 | Glidant | 12.5 |
| Mg stearate | Lubricant | 1.5 |
| Croscarmellose | Disintegrant | 13.0 |
| Syloid 244 FP | Glidant | 1.5 |
| Core total | | 270.0 |
| Coating | | |
| Opadry II white Coating system | | 11.0 |
| Total | | 281.0 |

*corresponding to 50 mg free base KdPT

The samples were packed in Alu/Alu blister under controlled climate conditions.

3.3 Results

The formulations containing MCC 101, sorbitol DC and Galen IQ 720 (isomalt) showed satisfying compression properties during direct compression. Trehalose was not compressible (no satisfying tablet hardness achievable). The finished tablets based on sorbitol, isomalt and MCC could be compressed to tablets with a resistance to crushing in the range of 50-80 N or even higher. The disintegration time for all formulations was not more than 5 minutes. The tablet with the highest stability is the one using MCC 101 as indicated in Table 6 above.

TABLE 7

| Comp. Ex. 2 | 0 months | 0.5 months | 1 month | 3 months |
|---|---|---|---|---|
| (%) | 0.35 | 0.49 | 0.62 | 1.19 |

The data obtained are % values of DKP based on the amount of KdPT free base.

It becomes evident from Table 7 that the amounts of DKP measured over a time period of already 3 months significantly increased in Comparative Example 2 (Comp. Ex. 2: 0.35 to 1.19% even after 3 months). These results clearly show the reduced storage stability of the non-lyophilized KdPT formulation, despite of a coating applied.

4. Preparation of a Pharmaceutical Composition

The lyophilisates of Examples 1-3 obtained as described under item 1. above were reconstituted by adding 5 mL WFI to form aqueous solutions, respectively, e.g. for oral administration. If desired, further conventional pharmaceutically acceptable excipients such as flavouring agents, pH adjusting agents and/or preservatives, may be added to the aqueous solution or, alternatively, to the WFI before reconstitution.

The invention claimed is:

1. A stable lyophilized formulation comprising:
Lysyl-Prolyl-Threonine or a pharmaceutically acceptable salt thereof, wherein the Lysyl-Prolyl-Threonine is present in an amount of about 0.1-50 mg free base, based on 100 mg total weight of the lyophilized formulation;
one or more bulking agents selected from the group consisting of mannitol, sucrose and trehalose, wherein the one or more bulking agents are present in an amount of about 30-95 mg, based on 100 mg total weight of the lyophilized formulation; and
one or more buffering agents selected from the group consisting of citric acid, sodium dihydrogenphosphate, acetic acid, succinic acid, glutamate, Tris and histidine, wherein the one or more buffering agents are present in an amount of about 0.5-50 mg, based on 100 mg total weight of the lyophilized formulation.

2. The lyophilized formulation according to claim 1, further comprising one or more pH adjusting agents.

3. The lyophilized formulation according to claim 1, prepared by lyophilizing an aqueous preparation having a pH of 3.0-5.0, wherein the aqueous preparation comprises:
(i) Lysyl-Prolyl-Threonine or a pharmaceutically acceptable salt thereof, wherein the free base has a concentration of 0.1-175 mg/g, based on the aqueous preparation,
(ii) aqueous carrier,
(iii) the one or more bulking agents, wherein the one or more bulking agents has a concentration of 50-175 mg/g, based on the aqueous preparation,
(iv) the one or more buffering agents, wherein the one or more buffering agents has a concentration of 1-100 mg/g, based on the aqueous preparation, and
(v) optionally one or more pH adjusting agents.

4. The lyophilized formulation according to claim 1, wherein the Lysyl-Prolyl-Threonine is (L)Lys-(D)Pro-(L)Thr, (L)Lys-(L)Pro-(D)Thr, (L)Lys-(D)Pro-(D)Thr, (L)Lys- (L)Pro-(L)Thr, (D)Lys-(D)Pro-(L)Thr, (D)Lys-(D)Pro-(D)Thr, (D)Lys-(L)Pro-(L)Thr, (D)Lys-(L)Pro-(D)Thr, or mixtures thereof.

5. The lyophilized formulation according to claim 2, wherein the pH adjusting agent is an acid or a base that maintains a pH value at 3.0-5.0 selected from sodium hydroxide and hydrochloric acid.

6. A medicament, comprising the lyophilized formulation according to claim 1.

7. A method of administering the medicament of claim 6 to a patient, wherein either the lyophilized formulation is administered to the patient in solid form, or the solid lyophilized formulation is reconstituted with an aqueous carrier to form an aqueous preparation, the aqueous preparation being subsequently administered to the patient.

8. A process for preparing the lyophilized formulation as defined in claim 1, comprising the steps of:
   (a) mixing in any order the following components:
      (i) Lysyl-Prolyl-Threonine or a pharmaceutically acceptable salt thereof,
      (ii) an aqueous carrier,
      (iii) the one or more bulking agents,
      (iv) the one or more buffering agents, and
      (v) optionally one or more pH adjusting agents;
   to provide for an aqueous preparation having a pH in the range of 3.0-5.0, wherein the free base of Lysyl-Prolyl-Threonine has a concentration of 0.1-175 mg/g, based on the aqueous preparation; and
   (b) lyophilizing the aqueous preparation to provide for the lyophilized formulation in solid form.

9. A lyophilized formulation prepared by the process of claim 8.

10. A pharmaceutical composition comprising the lyophilized formulation as defined in claim 1 and one or more pharmaceutical excipients.

11. The pharmaceutical composition according to claim 10, either in the form of an aqueous preparation prepared by reconstituting the lyophilized formulation with an aqueous carrier or in solid form.

12. A cosmetic composition comprising the lyophilized formulation as defined in claim 1 and one or more cosmetic excipients.

13. A method of cosmetic, non-therapeutic treatment of a patient, comprising administering the lyophilized formulation according to claim 1 to the skin and/or mucosa of a mammal.

14. A method of administering the medicament of claim 6 to a patient, comprising orally administering the formulation to the patient or injecting the formulation into the patient.

15. The pharmaceutical composition according to claim 11, wherein the composition comprises the lyophilized formulation in an aqueous carrier at a ratio of lyophilized formulation to aqueous carrier of 1:0.5 to 1:1000.

16. The lyophilized formulation of claim 1, wherein the bulking agent is sucrose.

17. The lyophilized formulation of claim 16, wherein the sucrose is present in an amount of 40-90 mg.

18. The lyophilized formulation of claim 1, wherein the bulking agent is trehalose.

19. The lyophilized formulation of claim 18, wherein the trehalose is present in an amount of 40-90 mg.

20. The lyophilized formulation of claim 16, wherein the sucrose is present in an amount of 40-75 mg.

21. The lyophilized formulation of claim 18, wherein the trehalose is present in an amount of 40-75 mg.

22. The lyophilized formulation of claim 1, wherein the buffering agent is citric acid.

23. The lyophilized formulation of claim 22, wherein the citric acid is present in an amount of 1-20 mg.

24. The lyophilized formulation of claim 23, wherein the citric acid is present in an amount of 5-15 mg.

* * * * *